Figure 1:
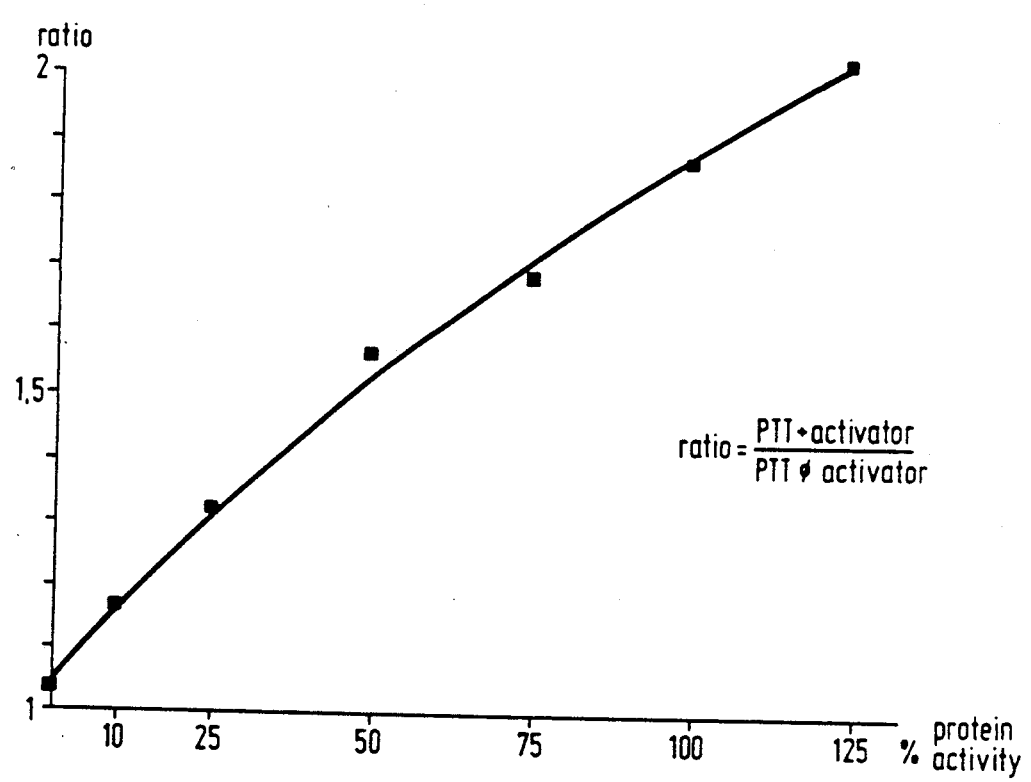

United States Patent [19]

Bartl et al.

[11] Patent Number: 5,001,069

[45] Date of Patent: Mar. 19, 1991

[54] PROCESS FOR PHOTOMETRIC DETERMINATION OF PROTEIN C AND/OR PROTEIN

[75] Inventors: Knut Bartl, Wilzhofen; Andreas Dessauer, Tutzing; Helmut Lill, Wielenbach, all of Fed. Rep. of Germany

[73] Assignee: Boehringer Mannheim GmbH, Mannheim, Fed. Rep. of Germany

[21] Appl. No.: 256,100

[22] Filed: Oct. 4, 1988

Related U.S. Application Data

[63] Continuation of Ser. No. 16,285, Feb. 19, 1987, abandoned.

[30] Foreign Application Priority Data

Mar. 7, 1986 [DE] Fed. Rep. of Germany ....... 3607559

[51] Int. Cl.$^5$ ..................... G01N 33/68; G01N 33/00
[52] U.S. Cl. ........................................ 436/86; 436/69; 435/13; 422/61
[58] Field of Search ...................... 435/13; 436/69, 87, 436/86; 422/61

[56] References Cited

U.S. PATENT DOCUMENTS

| 4,289,498 | 9/1981 | Baughman et al. ................. 436/34 |
| 4,334,018 | 6/1982 | Kirchhof . |
| 4,692,406 | 9/1987 | Becker et al. . |

FOREIGN PATENT DOCUMENTS

| 0076042 | 3/1982 | European Pat. Off. . |
| 0182929 | 4/1983 | European Pat. Off. . |
| 0107383 | 9/1983 | European Pat. Off. . |
| 0203509 | 8/1987 | European Pat. Off. . |

*Primary Examiner*—Robert J. Warden
*Assistant Examiner*—Lyle Alfandary-Alexander
*Attorney, Agent, or Firm*—Felfe & Lynch

[57] ABSTRACT

The present invention provides a process for the photometric determination of protein C and/or protein S activity, especially in plasma, wherein the sample containing the protein C and/or protein S to be determined is incubated with a protein C activator from snake venom with the formation of activated protein C and/or protein S and the decrease of the formation of thrombin from prothrombin brought about by the coagulation factors and the activators thereof is determined by means of a chromogenic thrombin substrate.

13 Claims, 1 Drawing Sheet

PROCESS FOR PHOTOMETRIC DETERMINATION OF PROTEIN C AND/OR PROTEIN

This application is a continuation of application Ser. No. 016,283, filed Feb. 19, 1987, now abandoned.

The present invention is concerned with a process for the photometric determination of protein C and/or protein S activity, especially in plasma.

Protein C is a double-chained, vitamin K-dependent glycoprotein in plasma which is synthesized in the liver. A physiologically indifferent coagulation precursor (decarboxy-protein C) is thereby first formed. Carboxylation of γ-glutamic acid residues in the protein by a vitamin K-dependent carboxylate results in the formation of protein C. Protein C itself is a pro-enzyme and is converted by thrombin into activated protein C. The latter acts as an anti-coagulant by a proteolytic inactivation of the activated coagulation factors V and VIII. The anti-coagulatory action of the active protein C is increased by a cofactor, protein S. Protein S is a single-chained glycoprotein in plasma which is also vitamin K-dependent. Active protein C and protein S form an equimolar complex. A lowered protein C level, as well as protein S level, have been described in patients with liver diseases, disseminated intravascular coagulation (DIC) and after warfarin therapy. A congenital deficiency of protein C or of protein S results in venous thromboembolic risks. Therefore, protein C, as well as protein S, play an important part not only in the case of physiological haemostasis but also in many diseases and especially in the case of thrombosis.

In the case of a commercially available test process, the amount of protein C in plasma is determined by enzyme-labelled antibodies. However, this process suffers from the disadvantage that the antibodies used for the determination also react with the above-mentioned decarboxy-protein C. Since the plasma concentration of decarboxyprotein frequently increases very considerably during-the course of a treatment with anticoagulants, this process involves a large source of error which, under certain circumstances, can result in a false or insufficient therapy.

The disadvantage in the case of the use of immunological determination processes for protein C in plasma is the fact that it provides no information about the biological activity of the protein C molecules. The presence of abnormal protein C with strongly reduced biological activity (genetic variants) cannot be found with such processes.

R. B. Francis and M. J. Patch (Thrombosis Research, 32, 605–613/1983) have described a process for the determination of activated protein C in human plasma by determination of the partial thromboplastin time (PTT test). The protein C separated from plasma by adsorption on barium citrate is thereby activated by the addition of thrombin and thereafter the latter is inhibited by an excess of antithrombin III and heparin. Heparin in turn is thereby neutralized by an exact amount of protamine sulphate which, in each case, has to be newly determined. Thereafter, protein C is determined via the partial thromboplastin time. The indicator reaction is here the cleavage of fibrinogen by thrombin and formation of a fibrin clot.

R. M. Bertina-et al. (Thromb. Haemostas., 51(1), 1-5/1984) describe a spectrophotometric process for the determination of protein C activity. This process involves three independent steps:

1. isolation of the protein C with the help of an aluminium hydroxide adsorption;
2. activation of the protein C separated from the plasma with thrombin, as well as subsequent inhibition of the latter by equimolar amounts of antithrombin III and heparin; and
3. measurement of the proteolytic activity of isolated, activated protein C with a chromogenic substrate ($S_{2366}$ = H-pyro-Glu-Pro-Arg-pNA).

This process is unsatisfactory with regard to the specificity for protein C since this substrate can also be split by other coagulation proteases. Thus, it can give falsely positive results.

In another photometric method of determination, use is made of the protein C activator Protac ®(producer Pentapharm, Switzerland), which is obtained from the venom of the snake *Agkistrodon contortrix contortrix*, as well as a chromogenic protein C substrate (2 AcOH. H-Pro-Pro-Arg-pNA). In the case of this process, the preparation of the sample can be omitted. However, with this process, it is not possible to differentiate between carboxylated and non-carboxylated protein C. However, it is known that only carboxylated protein C is effective in vivo. Therefore, no information about the biological activity of the protein C molecule can be obtained with this process.

In the case of another known process for the determination of protein C, Protac ® is also used as protein C activator. The protein C determination thereby takes place, after the addition of activators for the endogenic coagulation system, via a clotting test. With this process, it is admittedly possible to differentiate between carboxylated and non-carboxylated protein C but this process suffers from the disadvantage that the detection must take place via the coagulum formation (clotting). The determination is thereby limited to certain detection processes (for example the hook method or the magnetic field method) which, furthermore, have proved to be subject to disturbance and cannot be automated.

According to one of our earlier suggestions, the determination of protein C takes place in that activated protein C is first formed by the action of thrombin, this thrombin is thereafter inactivated and subsequently thrombin newly formed by the coagulation cascade is determined with the help of a synthetic thrombin substrate. In fact, there is thereby measured the slowing down of the thrombin formation in comparison with a carrying out of the test without protein C.

The amount of protein S in plasma can be determined in an immuno-radiometric test, such as that described, for example, by Bertina et al. (Thromb. Haemostas., 53 (2), 268–272/1985}. However, this process suffers from the disadvantage that the antibodies used for the determination also react with nonfunctional protein S, i.e. for example with decarboxyprotein S or with protein S complexed by $C_{4b}$-binding protein. Under certain circumstances, this results in falsely positive protein S values and thus in an insufficient therapy.

In the same article, the authors Bertina et al. also describe a possibility of how functional protein S from human plasma can be determined: if activated protein C is admixed with human plasma and subsequently the partial thromboplastin time (PTT) of this mixture is determined, then the PTT is the longer the greater is the concentration of functional protein S. The indicator reaction is here also the cleavage of fibrinogen by thrombin and the formation of a fibrin clot. The process is thus limited to certain detection processes which are subject to disturbance and, in general, cannot be automated. It has the further disadvantages that purified, activated protein C must be used and that protein C and protein S cannot be simultaneously determined in plasma.

It is an object of the present invention to provide a process for the photometric determination of biologically active protein C and/or protein S which is simpler to carry out than the above-mentioned known methods and can also be automated.

According to the present invention, there is provided a process for the photometric determination of protein C and/or protein S activity, especially in plasma, wherein the sample containing the protein C and/or protein S to be determined is incubated with a protein C activator from snake venom with the formation of activated protein C and/or protein S and the decrease of the formation of thrombin from prothrombin brought about by the coagulation factors and the activators thereof is determined by means of a chromogenic thrombin substrate.

Thus, for the determination of protein C and/or protein S, there are simultaneously added an activator for protein C from snake venom, an activator for the coagulation system and a chromogenic thrombin substrate and the action of protein C and protein S on the coagulation factors VIII and V is determined via the cleavage of the chromogenic thrombin substrate.

The present invention is based upon the surprising discovery that protein C activator from snake venom, in contradistinction to other protein C activators, does not split the thrombin substrate.

This was surprising because Protac, ® for example, is, in its action, a thrombin-like activator for protein C. Consequently, it was to have been expected that the chromogenic thrombin substrate would also be reacted by the snake venom activator or by the mixture of the activator with protein C because thrombin and other known protein C activators, for example plasmin and trypsin, react with the chromogenic thrombin substrate. Therefore, if such protein C activators are used, after activation of protein C the activator would have to be inactivated. Only subsequently could the activators for the coagulation system and the chromogenic thrombin substrate be added. However, in the case of the use of a protein C activator from snake venom, it has been shown, surprisingly, that this inactivation step can be omitted. It is even possible to add the activators for the coagulation system and the chromogenic thrombin substrate at the beginning of the determination.

As protein C activator, in the scope of the present invention there can be used solutions of snake venoms, for example of *Agkistrodon contortrix contortrix, A. C. mokasen, A. C. pictigaster, A. piscivours, A. p. leucostoma, A. bilineatus, Bothrops moojeni, B. pradoi, Cerastes cerastes, Vipera lebetrina* or *V. russellii*. However, it is preferred to use the protein C activator isolated from the snake venom of *Agkistrodon contortrix contortrix*.

Venoms or venom components are preferably used which also in plasma only activate protein C, the desired venom components being easily isolated from the venom of a snake. For this purpose, there can be employed the generally used processes, for example anion exchanger chromatography, affinity chromatography with protein C and/or ultra-filtration.

The activator is used in a concentration of 0.05 to 5 U/ml. and preferably of from 0.5 to 1 U/ml. activator solution. In this case, a unit (U) of protein C activator is defined as being the amount which fully activates the amount of protein C contained in 1 ml. of normal human citrate plasma at 37° C. and pH 7 to 8 in a reaction mixture of one part by volume of plasma and 4 to 8 parts by volume of aqueous protein C activator solution.

Since activated protein C (APC) proteolytically inactivates the coagulation factors V and VIII, whereby protein S functions as co-factor, in the case of the process according to the present invention, the coagulation system is preferably modified by the addition of activators for coagulation factors and/or of coagulation factors themselves in such a manner that the inactivation of factors V or VIII manifests itself in a reduction of the thrombin formation which is as marked as possible. According to a first embodiment of the process according to the present invention, this is preferably achieved by adding an activator for factor XII, for example ellagic acid together with cephalin. According to a second embodiment of this preferred variant, there is added an activator for factor VII, for example thromboplastin, and factor V. According to a third embodiment, as activator for factor II there is added factor Xa, together with cephalin. The buffer employed for this purpose, usually also contains calcium ions.

These preferred embodiments of the process according to the present invention take into account the fact that the concentrations of the coagulation parameters factors XII, XI, VIII, X, V and II influence the time of the thrombin formation in such a manner that a particular thrombin threshold value is achieved the sooner, the higher is the concentration of these factors.

In the scope of the present invention, the thrombin formation is determined according to known methods, the partial thromboplastin time (PTT) method being suitable for this purpose. In carrying it out, it is preferable to add an activator for factor XII. The thrombin formation can also be determined by the prothrombin time method. In this case, it is preferable to add an activator for factor VII and factor Va.

As chromogenic thrombin substrate, in the scope of the present invention there can be used any chromogenic substrate suitable for the determination of thrombin. However, in the scope of the present invention, it is preferred to use H-D-Phe-Pip-Arg-pNA or Tos-Gly-Pro-Arg-pNA, wherein pNA means p-nitroaniline. The pNA represents the chromogenic component of the substrate and is split off by the thrombin formed so that it can be determined photometrically in known manner.

As coagulation system, there can be used, for example, a mixture of factors II to XII or substrate plasma, for example plasma deficient in protein C or protein S.

In the scope of the present invention, use can be made of any plasma, citrate plasma being preferred.

The process can be carried out at neutral to weakly alkaline pH values and preferably at pH 6 to 9. As buffers, there can be used the physiologically compatible buffers which are effective in this pH range, for example tris/HCl. Furthermore, there can also be added the stabilizers and preservatives usual for coagulation tests, such as bovine serum albumin, merthiolate and the like.

With the process according to the present invention, protein C and protein S can be determined together or protein C or protein S can be determined alone.

If protein C and protein S are to be determined together, the patient's plasma can be used directly for the determination. If protein C alone is to be determined, apart from the reagent, protein S must also be added. This preferably takes place in the form of a plasma deficient in protein C but which contains protein S. The amount of protein S added must thereby be at least as large as the presumed protein C concentration. If protein S alone is to be determined, apart from the reagent, protein C must also be added. This preferably takes place in the form of a plasma deficient in protein S. Here, too, there must be added at least the same amount of protein C as the presumed protein S concentration.

Plasma deficient in protein S or protein C can be prepared by immune adsorption chromatography, for example in the manner described by R. M. Bertina et al., in Thromb. Haemostas., 51, 1–5/1984 or by Bertina et al. in Thrombosis and Haemostasis, 53, 268–272/1985.

The following Examples are given for the purpose of illustrating the present invention, reference being made to the accompanying drawing which illustrates a calibration curve for protein C activity determination, the ratio of the partial thromboplastin time with and without activator (ratio) being plotted against the percentage concentration of protein C in plasma.

EXAMPLE 1

Preparation of a highly purified protein C activator preparation from A. contortrix venom 1 g. of *A. contortrix* venom is dissolved in 100 ml. water, the pH value of this solution is adjusted with 0.3 mole/liter orthophosphoric acid to 3.0 and the acidic venom solution is maintained for 10 minutes in a water-bath at 70±2° C., subsequently cooled to 20° C., the pH value is adjusted with aqueous sodium hydroxide solution (1 mole/litre) to 7.2, the turbid solution is centrifuged and the supernatant is diluted with distilled water to a volume of 100 ml. in order thus to obtain a pre-purified venom fraction.

The pre-purified venom fraction is applied to a column of DEAE-Sephadex A-50 with the dimensions of 2.6×90 cm. equilibrated with 0.015 mole/litre sodium phosphate buffer (pH 6.8) and eluted with a linear gradient mixed from 0.015 mole/litre sodium phosphate buffer (pH 6.8) and 0.4 mole/litre sodium chloride in 0.015 mole/litre sodium phosphate buffer (pH 6.8) and 20 ml. fractions are collected. The protein C-activating action of the individual fractions is determined by mixing 0.1 ml. human citrate plasma with 0.1 ml. sample (fraction diluted with water 1:350 v/v) and 0.1 ml. sample ellagic acid reagent (Actin) ® and 0.1 ml. 0.025 mole/litre calcium chloride solution, a stop watch is immediately started and the time up to coagulation is determined. The samples containing protein C activator bring about a prolongation of the coagulation time from 34 seconds to up to 200 seconds, depending upon the activator content.

The protein C-containing fractions are combined, concentrated by ultrafiltration to one tenth of the eluate volume, taken up in 0.05 mole/litre sodium acetate buffer (pH 5.0) and applied to a column of CM-Sephadex C-50 equilibrated with 0.01 mole/litre sodium acetate buffer (pH 5.0) and eluted with a linear gradient mixed from 0.05 mole/litre sodium acetate buffer (pH 5.0) and 0.4 mole/litre sodium chloride in 0.05 mole/-litre sodium acetate buffer (pH 5.0) and 20 ml. fractions are collected which are tested for protein C-activating action according to the above-described method.

The protein C-activating fractions are mixed together, concentrated by ultrafiltration to 1/25th of their volume, made up to 25 ml. with 1% acetic acid in distilled water and applied to a column of Sephadex G-100 equilibrated with 1% acetic acid in water, eluted with 1% acetic acid and 20 ml. fractions collected which are again tested for protein C-activating action according to the initially described method.

The protein C-activating fractions are combined and lyophilized, a salt-free activator preparation being obtained which, in polyacrylamide gel electrophoresis, only shows a single zone and a protein C-activating activity of 35 U per mg.

One unit (U) of protein C activator is the amount which completely activates the amount of protein C contained in 1 ml. of normal human citrate plasma.

EXAMPLE 2

Measurement of activated protein C by means of the prolongation of the partial thromboplastin time in the presence of protein C activator according to Example 1.

25 μl. diluted plasma sample (1+4 with 0.9% aqueous sodium chloride solution), 25 μl. protein Cdefective normal plasma and 500 μl. of reagent, consisting of cephalin and ellagic acid in 10 mmole/liter tris/HCl (pH 7.6), are incubated in a plastic cuvette at 37° C. After precisely 1 minute, either
1. 20 μl. protein C activator according to Example 1 (concentration: flask contents =3 U in 3 ml. 0.9% aqueous sodium chloride solution) or
2. 20 μl. 0.9% aqueous sodium chloride solution are added thereto, mixed and further incubated.

After precisely 4 minutes, 150 μl. of starting reagent, consisting of 1.1 mmole/litre Chromozym ® TH (Tos-Gly-ProArg-pNA) and 100 mmole/litre calcium acetate, are added thereto and at 405 nm there is determined in a photometer the time until a definite amount of substrate is reacted by newly formed thrombin to give Tos-Gly-Pro-Arg and p-nitroaniline (pNA). The amount of reacted substrate, which is measured, is defined by a threshold extinction value (for example $\Delta E = 0.2$).

Under the given conditions, the partial thromboplastin time increases proportionately with the concentration of protein C in the plasma sample when the activator Protac ® is added to the mixture. Since the partial thromboplastin time is dependent, inter alia, upon the factor content of plasma, it is preferred to measure at the same time a blank with 0.9% aqueous sodium chloride solution. The ratio of PTT time with activator to PTT time without activator is a measure of the protein C content. Via a calibration curve, which is obtained with plasma samples of different, known protein C concentrations, the protein C concentration of the unknown plasma sample can be determined. The following Table contains three examples of plasma samples of unknown protein C concentration.

TABLE 1

| Prolongation of the PTT time by activated protein C in plasma dilutions and plasma samples | | | |
|---|---|---|---|
| sample | antigen+ | ratio with/without protein C activator according to Example 1 | activity |
| standard 1 | 125% | 2.01 | 125% |

TABLE 1-continued

Prolongation of the PTT time by activated protein C in plasma dilutions and plasma samples

| sample | antigen+ | ratio with/without protein C activator according to Example 1 | activity |
|---|---|---|---|
| standard 2 | 100% | 1.86 | 100% |
| standard 3 | 75% | 1.68 | 75% |
| standard 4 | 50% | 1.56 | 50% |
| standard 5 | 25% | 1.32 | 25% |
| standard 6 | 10% | 1.17 | 10% |
| protein C defective plasma | 0% | 1.04 | 0% |
| control plasmas | 114% | 1.94 | 114% |
|  | 81% | 1.70 | 75% |
|  | 23.5% | 1.27 | 22% |

+with ELISA test of Boehringer Mannheim GmbH

We claim:

1. Method for photometric determination of at least one of active protein C and active protein S in a sample comprising simultaneously incubating the sample with a protein C activator from snake venom which activates protein C and/or protein S, a chromogenic thrombin substrate and a coagulation system activator and determining cleavage of said chromogenic thrombin substrate by thrombin as an indicator of active protein C and/or protein S in said sample, without adding an inactivator of said protein C activator.

2. Method according to claim 1 wherein the protein C activator is a solution of venom of Agkistrodon contortrix contortrix or of components of said venom which activate protein C.

3. Method according to claim 1, wherein the protein C activator is venom of *A. C. mokasen, A. C. pictigaster, A. piscivours, A. p. leucostoma, A. bilineatus, Bothrops moojeni, B. pradoi Cerastes cerrastes, Vipera lebetrina* or *V. russellii.*

4. Method according to claim 1, wherein the chromogenic thrombin substrate used is H-D-Phe-Pip-Arg-pNA or Tos-Gly-Pro-Art-pNA.

5. Process according to claim 1 further comprising adding protein C deficient plasma to said sample.

6. Method according to claim 1 further comprising adding protein S deficient plasma to said sample.

7. Method of claim 1, wherein said sample is a plasma sample.

8. Method according to claim 1, further comprising adding an activator for factor XII to said sample.

9. Method according to claim 8, wherein said factor XII activator is cephalin and ellagic acid.

10. Method according to claim 1 further comprising adding an activator for factor VII to said sample.

11. Method according to claim 10, wherein said factor VII activator is factor V and thromboplastin.

12. Method according to claim 1 further comprising adding an activator for factor II to said sample.

13. Method according to claim 12, wherein said factor II activator is cephalin and factor Xa.

* * * * *

UNITED STATES PATENT AND TRADEMARK OFFICE
CERTIFICATE OF CORRECTION

PATENT NO. : 5,001,069

DATED : March 19, 1991

INVENTOR(S) : Knut Bartl et al.

It is certified that error appears in the above-identified patent and that said Letters Patent is hereby corrected as shown below:

On the title page:
In the "Related U.S. Application Data", please change "16,285" of the continuation Serial No. to -- 16,283 --.

Signed and Sealed this

Fifth Day of January, 1993

*Attest:*

DOUGLAS B. COMER

*Attesting Officer*      *Acting Commissioner of Patents and Trademarks*